United States Patent
Digiacomantonio et al.

(10) Patent No.: US 7,811,271 B2
(45) Date of Patent: Oct. 12, 2010

(54) ABSORBENT ARTICLE HAVING FLAP ACTIVATION

(75) Inventors: Marco Digiacomantonio, Pescara (IT); Giovanni Carlucci, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 847 days.

(21) Appl. No.: 11/484,963

(22) Filed: Jul. 12, 2006

(65) Prior Publication Data

US 2008/0015536 A1    Jan. 17, 2008

Related U.S. Application Data

(60) Provisional application No. 60/715,510, filed on Sep. 9, 2005.

(51) Int. Cl.
*A61F 13/15*    (2006.01)
(52) U.S. Cl. ............... 604/385.04; 604/385.28; 604/385.22; 604/385.16; 604/385.01
(58) Field of Classification Search ........... 604/385.04, 604/385.28, 385.22, 385.16, 385.01
See application file for complete search history.

(56) References Cited

U.S. PATENT DOCUMENTS

| 3,397,697 | A | 8/1968 | Rickard |
|---|---|---|---|
| 4,285,343 | A | 8/1981 | McNair |
| 4,589,876 | A | 5/1986 | Van Tilburg |
| 4,605,404 | A | 8/1986 | Sneider |
| 4,608,047 | A | 8/1986 | Mattingly |
| 4,692,163 | A | 9/1987 | Widlund |
| 4,701,177 | A | 10/1987 | Ellis |
| 4,900,320 | A | 2/1990 | McCoy |
| 4,911,701 | A | 3/1990 | Mavinkurve |
| 4,917,697 | A | 4/1990 | Osborn, III |
| 4,940,462 | A | 7/1990 | Salerno |
| 4,950,264 | A | 8/1990 | Osborn, III |
| 5,125,918 | A | 6/1992 | Seidy |
| 5,133,704 | A | 7/1992 | Wheeler |
| 5,267,992 | A | 12/1993 | VanTilburg |
| D348,514 | S | 7/1994 | Pearlstein |

(Continued)

FOREIGN PATENT DOCUMENTS

EP    0 130 848 B1    11/1987

(Continued)

OTHER PUBLICATIONS

PCT International Search Report dated Feb. 14, 2007.

*Primary Examiner*—Jacqueline F. Stephens
(74) *Attorney, Agent, or Firm*—Amanda T. Barry; Andrew J. Hagerty; Gary J. Foose

(57) ABSTRACT

An absorbent article such as a sanitary napkin, adult incontinence device, or the like. The absorbent article has a pair of flaps for securing the absorbent article. The flaps extend laterally outward from the main body portion of the article. The flaps are associated with the main body portion at a juncture along the longitudinal edges of the main body portion. The flaps have a notch. The flaps have at least one first zone of anisotropic stiffness contiguous with the notch. The first zone of anisotropic stiffness has a relatively stiffer direction and a relatively less stiff direction. The first zone of anisotropic stiffness can be made of corrugated or ring-rolled portions of the absorbent article.

19 Claims, 5 Drawing Sheets

U.S. PATENT DOCUMENTS

| | | | |
|---|---|---|---|
| 5,330,461 A | 7/1994 | Leeker | |
| 5,344,416 A | 9/1994 | Niihara | |
| 5,354,400 A | 10/1994 | Lavash et al. | |
| 5,389,094 A | 2/1995 | Lavash | |
| 5,429,633 A | 7/1995 | Davis | |
| 5,518,801 A | 5/1996 | Chappell | |
| 5,558,657 A | 9/1996 | Hammons | |
| 5,591,153 A | 1/1997 | Mattingly, III | |
| 5,650,223 A | 7/1997 | Weinberger | |
| 5,670,004 A | 9/1997 | Mattingly, III | |
| 5,891,121 A | 4/1999 | Redwine et al. | |
| 5,993,431 A | 11/1999 | McFall et al. | |
| 6,077,255 A | 6/2000 | Hunter | |
| 6,689,112 B1 | 2/2004 | Blanchard et al. | |
| 2004/0068244 A1 | 4/2004 | Salone et al. | |
| 2005/0182374 A1 * | 8/2005 | Zander et al. | 604/380 |

FOREIGN PATENT DOCUMENTS

| | | |
|---|---|---|
| EP | 0 606 358 B1 | 7/1994 |
| EP | 0 511 905 B1 | 8/1995 |
| EP | 0 695 542 A1 | 2/1996 |
| EP | 0 755 235 B1 | 3/1999 |
| GB | 2 168 253 A | 6/1986 |
| JP | 40-036391 | 12/1965 |
| WO | WO 93/01785 A1 | 2/1993 |
| WO | WO 95/20931 A1 | 8/1995 |
| WO | WO 95/28137 A2 | 10/1995 |
| WO | WO 96/23472 | 8/1996 |
| WO | WO 97/03630 A1 | 2/1997 |
| WO | WO 97/12576 A1 | 4/1997 |
| WO | WO 97/21411 A1 | 6/1997 |
| WO | WO 97/41818 A1 | 11/1997 |
| WO | WO 97/47266 | 12/1997 |
| WO | WO 99/03436 | 1/1999 |
| WO | WO 01/72254 A2 | 10/2001 |

* cited by examiner

ABSORBENT ARTICLE HAVING FLAP ACTIVATION

CROSS REFERENCE TO RELATED APPLICATIONS

This application claims the benefit of U.S. Provisional Application Ser. No. 60/715,510, filed Sep. 9, 2005.

FIELD OF THE INVENTION

The present invention relates to absorbent articles such as sanitary napkins, adult incontinence devices, and the like. Still more particularly, the present invention concerns absorbent articles having flaps with a notch and a first zone of anisotropic stiffness for assisting in transferring the force applied by the wearer through the flaps when the flaps are folded down and under a wearer's undergarment and attached to the underside of the undergarment.

BACKGROUND OF THE INVENTION

All manner and variety of absorbent articles configured for the absorption of body fluids such as menses, urine, and feces are, of course, well known. Absorbent articles, particularly sanitary napkins, having wings or flaps are disclosed in the literature and are available in the marketplace.

Generally, the flaps extend laterally from a central absorbent means and are intended to be folded around the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties.

The flaps serve at least two purposes. First, the flaps prevent exudates which otherwise would soil the edges of the wearer's panties from doing such. Second, the flaps help stabilize the napkin from shifting out of place, especially when the flaps are affixed to the underside of the panties.

Sanitary napkins having flaps of the various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957. Often flaps are coated with an adhesive to assist in fixing the absorbent article to the wearer's panty.

When the flaps are folded down along the edges of the wearer's panties, stresses are created in the flaps. The stresses are especially high along the bending line at the edges of the wearer's panties where the flaps are bent from the bodyside of the panty to the underside of the panty. These stresses are caused by fitting a flap around the curved outline of a panty crotch. These stresses are magnified when a wearer sits or crouches because the edges of the panties are pulled outward against the flaps thus increasing the forces against this bending line. When the stresses become too high, the flaps may become detached from the panty and some portion of the aforementioned benefits of the flaps may be lost. In addition, even if the stresses are not sufficient to detach the flaps, they may still be sufficient to cause the flaps to bunch longitudinally inward. This effectively reduces the size of the flaps and the area of the wearer's undergarments that the flaps are able to cover. One approach to relieving these stresses is to provide flaps that have stress release means for relieving the stresses that develop in the flaps.

While sanitary napkins having flaps that include stress release means are viewed as providing better fit with the panty and better protection against soiling as compared to sanitary napkins without stress release means in the flaps, sanitary napkins having flaps that include stress release means commonly experience problems that keep them from being optimally effective. One problem is that when the wearer applies forces to the flaps to fold the flaps down and under the wearer's undergarment, individual flaps can fail to fold as a single unit. As a result, the portion of a flap that is folded adheres to the wearer's panty. The wearer then folds the remainder of the flap and attaches the flap to the panty. This multi-step process that is sometimes used by wearer's to attach a single flap to the wearer's panty can result in bunching and wadding of the flap, improper location of the absorbent article relative to the wearer's body, and failure of the flap to securely attach the absorbent article to the wearer's panty.

One possible solution to the problem of flaps failing to fold as a single unit is to make the flap out of a stiffer material. However, this solution may not be preferred because the absorbent article is worn in the crotch area of the wearer and as the wearer moves, the wearer's panty to which the absorbent article is attached moves and the absorbent article itself moves. Furthermore, the absorbent article can be in contact with the wearer's body and affect how the wearer's panty fits the wearer's body. Given the location where the wearer wears the absorbent article, more flexible materials are likely preferred by wearers over rigid inflexible materials because these materials may have less effect on the fit of the wearer's panty and can be more comfortable when worn in the crotch of the wearer. Additionally, using a stiffer material to construct the flaps is counter to the need to have flap materials that have stress release means to relieve the stress from folding the flap beneath the panty.

Ideally, the flaps could be relatively stiffer in particular directions so as to allow each flap to fold as a single unit when the user applies force to fold the wing yet still be relatively less stiff in other directions so as to allow stresses developed from folding the flap beneath the panty to be relieved and allow the absorbent article to be worn comfortably.

Another complicating problem is that the shape of the panty line in the wearer's crotch is often curved. Moreover, the curvature of the panty line in the wearer's crotch may vary from the portion of the panty generally oriented towards the wearer's front and the portion of the panty generally oriented towards the wearer's rear. Thus, as the flap of a sanitary napkin is folded underneath the wearer's panty, non-uniform stresses can develop along the bending line of the flap. The non-uniform stresses can impede the bending line of the flap in the engaged position from conforming to the panty line in the wearer's crotch region and result in the same problems as above including failure of the flap to attach to the wearer's panty, bunching and wadding of the flap, and an improperly located sanitary napkin.

Thus, there is a continuing unaddressed need for flaps that each fold as a single unit and have the desired ability to relieve stresses developed as a result of folding the flap beneath the wearer's panty.

Furthermore, there is a continuing unaddressed need for flaps having relatively less stiff areas that are oriented with lines of the wearer's panty to allow the wearer to install the flap such that the shape of the bending line of flap in the folded position conforms to the shape of the wearer's panty and have the ability to relieve stresses developed as a result of folding the flap beneath the wearer's panty.

SUMMARY OF THE INVENTION

In accordance with the present invention, an absorbent article, such as a sanitary napkin, having flaps with a combination of a notch and first zone of anisotropic stiffness for transmitting force applied to the flap by the wearer when the flaps are folded down along the edges of the wearer's panties in the crotch, is provided in accordance with the appended claims.

The sanitary napkin has a principal longitudinal centerline, a transverse centerline, and a flap transverse centerline. The principal longitudinal centerline and flap transverse centerline have an intersection. The sanitary napkin has a front area and a back area divided by the flap transverse centerline. The sanitary napkin has a left side and a right side that are generally disposed along the transverse centerline.

The sanitary napkin has a main body portion and a pair flaps associated with the main body portion. The main body portion of the sanitary napkin has a liquid pervious topsheet, a liquid impervious backsheet joined to the topsheet, and an absorbent core positioned between the topsheet and the backsheet. The main body portion has two spaced apart longitudinal edges and two spaced apart end edges. The flaps extend laterally outward from the main body portion. The flaps are associated with the main body portion at a juncture along the longitudinal edges of the main body portion. The flaps are divided into a front half and a back half by a flap transverse centerline. The flaps have a notch remote from the juncture. The flaps have at least one first zone of anisotropic stiffness located contiguous with the notch. The first zone of anisotropic stiffness has a relatively stiffer direction and a relatively less stiff direction. The relatively stiffer direction is parallel with an angle fifteen to forty five degrees off of the flap transverse centerline on the side on which the first zone of anisotropic stiffness is located. The vertex of the angle is the intersection of the longitudinal centerline and the flap transverse centerline and the rotation angle is measured towards the longitudinal centerline in the area in which the first zone of anisotropic stiffness is located.

The flap may have a pair of first zones of anisotropic stiffness. The first zones of anisotropic stiffness may be spaced from one another. The first zones of anisotropic stiffness may be made by corrugated or ring rolled portions of the absorbent article.

DETAILED DESCRIPTION OF THE INVENTION

Figure 1:
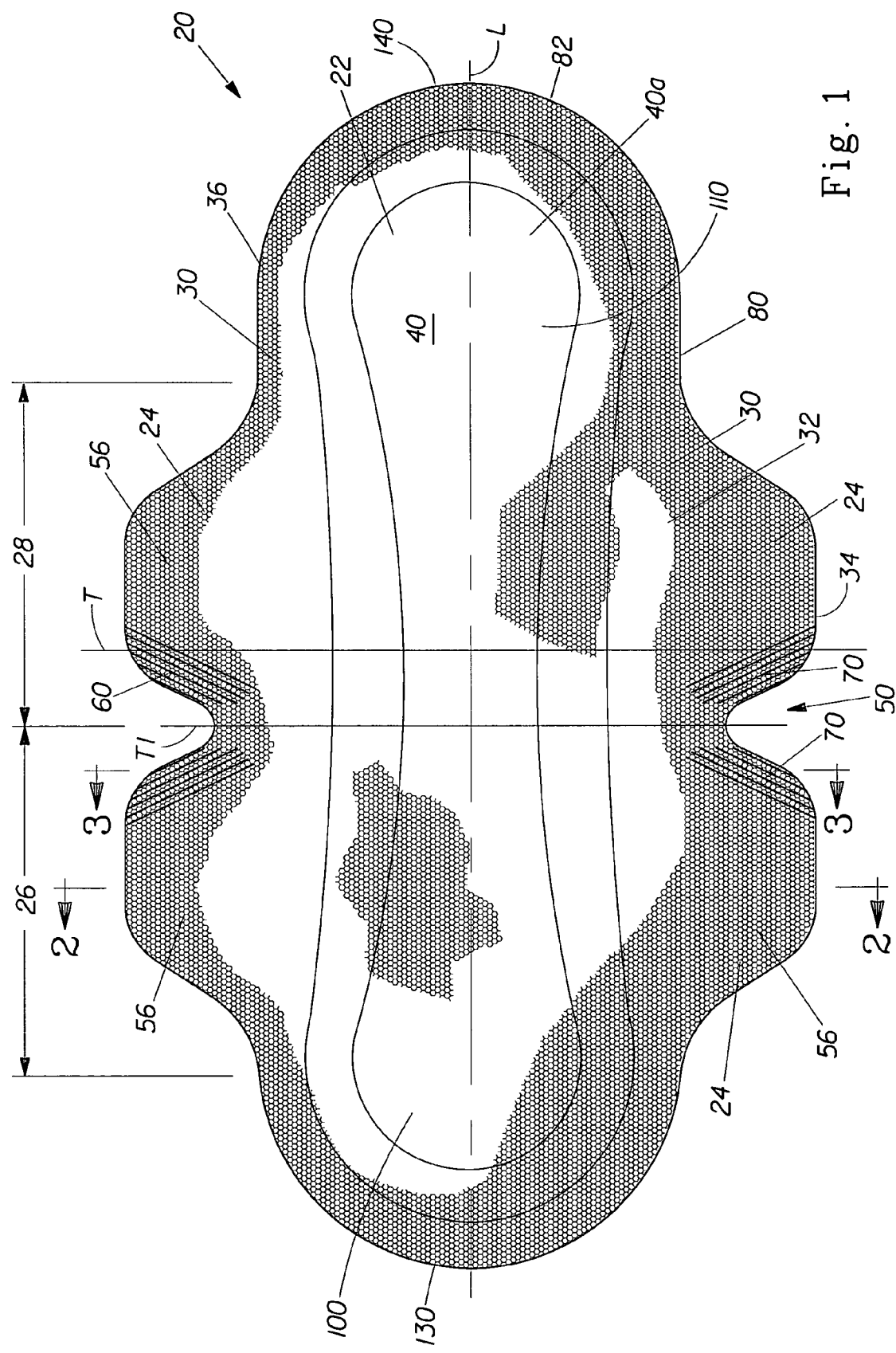
FIG. 1 is a top plan view of a sanitary napkin embodiment of the present invention.

All documents cited are, in relevant part, incorporated herein by reference; the citation of any document is not to be construed as an admission that it is prior art with respect to the present invention.

The present invention relates to absorbent articles such as sanitary napkins, adult incontinence devices, and the like. Still more particularly, the present invention concerns absorbent articles having flaps with a notch and a first zone of anisotropic stiffness for assisting in transferring the force applied by the wearer through the flaps when the flaps are folded down and under a wearer's undergarment and attached to the underside of the undergarment.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinent pads (and other articles worn in the crotch region of a garment). The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) In the preferred-embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

The term "anisotropic", as used herein, means exhibiting properties with different values when measured in different directions.

The term "stiffness", as used herein, refers to bending stiffness.

The term "vertex", as used herein, refers to the point about which an angle is measured.

As used herein, the term "indicia" refers to markings or indications that can be used to convey a message. Indicia can be a single color, a graphic, text, an arrow, a single dot, or any combination thereof.

A sanitary napkin 20 according to the present invention is shown in FIG. 1. As shown in FIG. 1, the sanitary napkin 20 basically comprises an absorbent means represented by central absorbent pad (or "main body portion") 22, and two flaps 24. In the discussion that follows, unless otherwise noted, the sanitary napkin described herein will have two flaps. While it is not necessary that the napkin have two flaps, two flaps are preferred over one flap. Also, while it is not necessary that the flaps be mirror images of one another, they preferably are mirror images of one another. Thus, the description of one flap will be a description of the other, and, for clarity, discussion of the second flap may be omitted.

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

Figure 2:
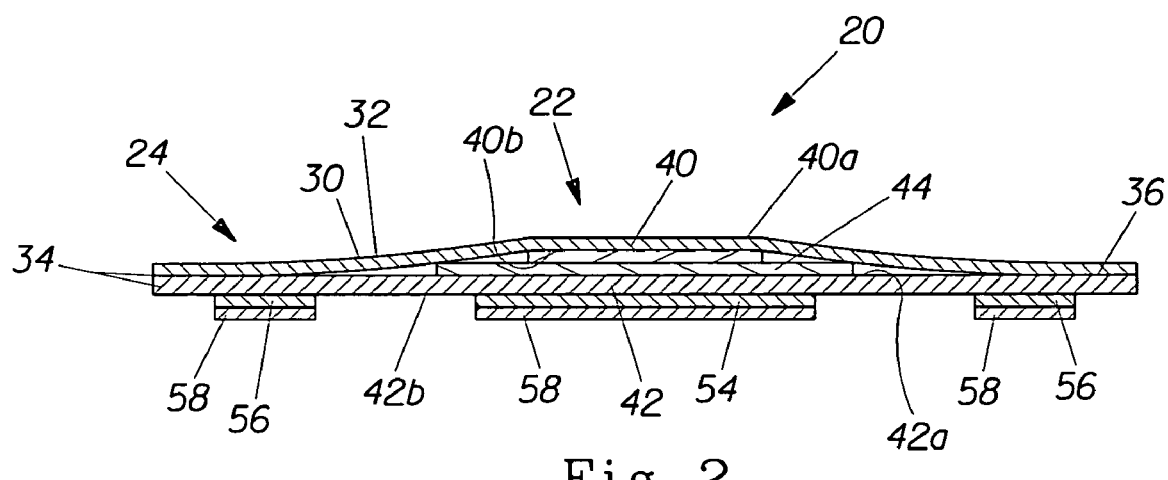
FIG. 2 is a cross-sectional view taken along line 1A-1A of FIG. 1.
Figure 3:
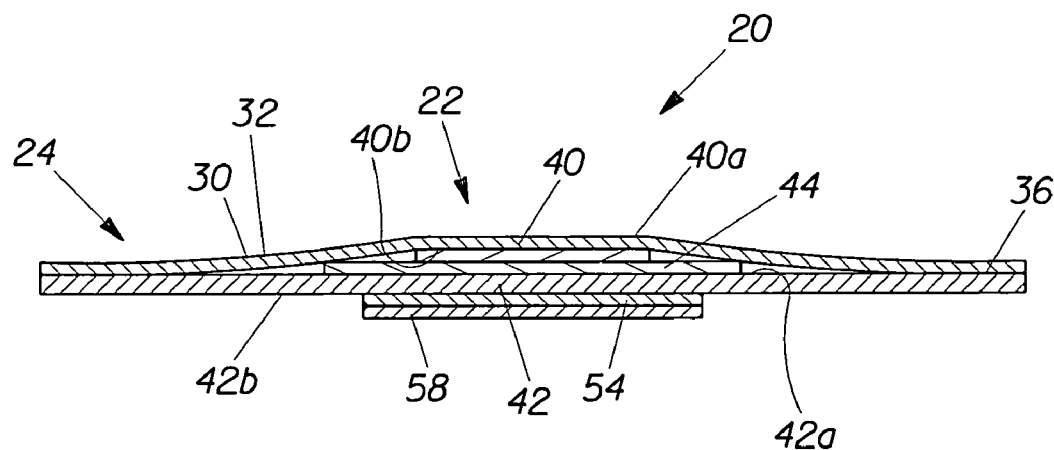
FIG. 3 is a cross-sectional view taken along line 1B-1B of FIG. 1.

Referring now to FIGS. 1, 2 and 3, the sanitary napkin 20 is comprised of a topsheet 40, a backsheet 42, an absorbent core 44, and a pair of flaps 24. At least a part of the topsheet 40, backsheet 42, and absorbent core 44 comprise the main body portion 22.

The topsheet 40 is liquid permeable and when the sanitary napkin 20 is in use, the topsheet 40 is in close proximity to the skin of the user. The topsheet 40 is compliant, soft feeling, and non-irritating to the user's skin. It can be made from any of the materials conventional for this type of use. Nonlimiting examples of suitable materials that can be used as topsheet 40 are woven and nonwoven polyester, polypropylene, 7 nylon, and rayon and formed thermoplastic films, with formed films being preferred.

Suitable formed films are described in U.S. Pat. No. 3,929, 135, entitled "Absorptive Structure Having Tapered Capillaries", which issued to Thompson on Dec. 30, 1975, U.S. Pat. No. 4,324,426, entitled "Disposable Absorbent Article Having A Stain-Resistant Topsheet", which issued to Mullane and Smith on Apr. 13, 1982, U.S. Pat. No. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which issued to Ahr, Louis, Mullane, and Ouellette on Jul. 31, 1984. Formed films are preferred for topsheet 40 because they are pervious to liquids and yet non-absorbent. Thus, the surface of the formed film which is in contact with the body remains dry and is more comfortable to the wearer.

In addition, in preferred embodiments of the present invention, at least a portion of the outer surface 40a of the topsheet 40 is treated with a surfactant. It is preferred that the surfactant be substantially evenly and completely distributed across at least the portion of the outer surface 40a of topsheet 40 that overlays the main body portion 22. This can be accomplished by any of the common techniques well known to those skilled in the art. For example, the surfactant can be applied to topsheet 40 by spraying, by padding, or by the use of transfer rolls.

Treating the outer surface 40a of the topsheet 40 with a surfactant renders the surface of the topsheet 40 more hydrophilic. This results in liquid penetrating the topsheet 40 faster than it would if the surface were not treated. This diminishes the likelihood that menstrual fluids will flow off topsheet 40 rather than being absorbed by the absorbent core 44. Preferably, any portions of the topsheet 40 that overlay the flaps 24 are not treated with the surfactant. This will minimize any tendencies fluids may have to spread laterally across the flaps and to come in contact with the wearer's thighs and other parts of the wearer's body.

In preferred embodiments, the inner surface 40b of topsheet 40 is secured in contacting relation with the absorbent core 44. This contacting relationship results in liquid penetrating topsheet 40 faster than if the topsheet 40 were not in contact with absorbent core 44. The topsheet 40 can be maintained in contact with absorbent core 44 by applying adhesive to the inner surface 40b of the topsheet 40. Suitable adhesives useful for this purpose are described in U.S. Pat. No. 4,917, 697. The adhesives can be applied by the same methods as the surfactant is applied to the outer surface 40a of the topsheet 40.

The absorbent core 44 is positioned between the topsheet 40 and the backsheet 42. The absorbent core 44 provides the means for absorbing menstrual fluid. The absorbent core 44 need not have an absorbent capacity much greater than the total amount of menstrual fluid anticipated to be absorbed. The absorbent core 44 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibers, polymeric fibers, hydrogel-forming polymer gelling agents, peat moss, or any equivalent material or combinations of materials.

Polymeric gelling agents are those materials which, upon contact with fluids (i.e., liquids) such as water or body fluids, imbibe such fluids and thereby form hydrogels. In this manner, fluids discharged into the absorbent core 44 can be acquired and held by the polymeric gelling agent, thereby providing the articles herein with enhanced absorbent capacity and/or improved fluid retention performance.

The polymeric gelling agent which is employed in the absorbent core 44 will generally comprise particles of a substantially water-insoluble, slightly cross-linked, partially neutralized, hydrogel-forming polymer material. The term "particles", as used herein, can refer to particles in any form, such as in the form of pellets, flakes, or fibers. The characteristics of the absorbent core 44 (including, but not limited to the preferred types of polymer materials used therein, and types of methods which can be used for preparing these polymer particles) are described in greater detail in U.S. Pat. No. 5,009,653 issued to Osborn and the patents incorporated by reference in that patent.

In one embodiment, the absorbent core 44 is a laminate comprised of a layer of superabsorbent polymer material, such as in the form of particles, disposed between two air-laid tissues, first and second tissue layers (or "upper" and "lower" tissue layers). The first and second tissue layers provide containment of the superabsorbent polymer material, improve lateral wicking of the absorbed exudates throughout the absorbent core 44 and provide a degree of absorbency.

A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012 entitled "Composition For Absorbent Film And Method Of Preparation", which issued to Pedersen et al. on Aug. 21, 1984, and U.S. Pat. No. 4,260,443 entitled "Laminated Absorbent Process", which issued to Lindsay et al. on Apr. 7, 1981.

The backsheet 42 is impervious to liquids and, thus, prevents menstrual fluid from soiling the clothing of the user. Any material used in the art for such purpose can be utilized herein. Suitable materials include embossed or nonembossed polyethylene films and laminated tissue. A suitable polyethylene film is manufactured by Monsanto Chemical Corporation and marketed in the trade as Film No. 8020.

In one alternative embodiment of the sanitary napkin 20 (typically in which the topsheet 40 overlays only the main body portion 22 and does not extend out to form the top surface of the flaps), the backsheet 42 may be comprised of two layers. In such a case, the backsheet 42 may comprise a first layer of lofted material disposed on the core-facing side 42a of the backsheet. The purpose of the first layer is to provide a comfortable, non-irritating surface against the body of the wearer. The lofted layer may be comprised of any suitable material, such as a nonwoven material. Preferably, the lofted layer comprises a hydrophobic nonwoven material. The second layer may be disposed on the garment side 42b of the backsheet 42, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Ethyl Corporation, Visqueen Division, under model XP-39385 has been found particularly well suited for this second layer. The backsheet 42 may also be made of a soft, cloth-like material which is hydrophobic relative to the topsheet 40. A polyester or polyolefinic fiber backsheet 42 has been found to work well. A particularly preferred soft, cloth-like backsheet 42 material is a laminate of a polyester nonwoven material and a film such as described in U.S. Pat. No. 4,476,180 issued to Wnuk on Oct. 9, 1984.

The topsheet 40 is joined or secured to backsheet 42 along a seam 36. The seam 36 can be formed by any means commonly used in the art for this purpose such as by gluing, crimping, or heat-sealing. The topsheet 40 may also be indirectly joined to the backsheet 42.

The main body portion 22 is the portion of the sanitary napkin 20 that contains an absorbent means, such as absorbent core 44. The main body portion 22 has a liquid pervious body contacting surface and an opposed liquid impervious surface. It is to be understood that the embodiment illustrated is only one possible embodiment, albeit a preferred one. Other possible embodiments include one in which an absorbent core 44 is essentially completely wrapped with topsheet before it is placed on a backsheet. The main body portion 22 can also comprise an absorbent core which possesses sufficient integrity to stand alone and is liquid pervious on one surface while the other surface has been treated to render it liquid impervious.

The main body portion 22 may be relatively thick or relatively narrow and thin. A narrow main body portion 22 may be effective because the overall configuration and use of sanitary napkin 20 results in main body portion 22 being maintained in close proximity to the body. Such proximity of main body portion 22 places it precisely where it should be: very near the body at the vaginal opening. The main body portion 22 can then absorb the vast majority of the menstrual fluid (menses) before it has an opportunity to flow along the sides of the main body portion 22. A thin main body portion may also be desired because it is typically comfortable to the user.

Fasteners, such as adhesive attachment means, central pad adhesive 54 and flap adhesive 56, are provided to secure the sanitary napkin 20 to the crotch region of an undergarment.

The central pad adhesive 54 provides an adhesive attachment means for securing main body portion 22 in the crotch portion of a panty. The outer surface of flap 24, adjacent the distal edge 34 of the flap, is preferably coated with a flap adhesive 56. The flap adhesive 56 is used to assist in maintaining the flap 24 in position after it is wrapped around the edge of the crotch portion of the panty as described below. The flaps 24 can be maintained in position by attaching the flaps 24 to the undergarment, or to the opposing flap. Suitable adhesive fasteners are described in greater detail in U.S. Pat. No. 4,917,697.

As shown, each flap 24 comprises a pair of flap adhesives. One flap adhesive 56 is positioned in the front half 26 of flap 24 while the other flap adhesive 56 is positioned on the back half 28 of flap 24. While a pair of flap adhesives 56, one positioned in the front half 24 and the other positioned in the back half 28 are preferred, other embodiments, having a single flap adhesive 56 may also be used. Other embodiments having three or more flap adhesives 56 may also be used.

The fasteners used with the present invention are not limited to adhesive attachment means. Any type of fastener used in the art can be used for such purpose. For example, the sanitary napkin 20 could be secured to the wearer's undergarment by the fastener described in U.S. Pat. No. 4,946,527 entitled "Pressure-Sensitive Adhesive Fastener and Method of Making the Same" issued to Battrell on Aug. 7, 1990. For simplicity, however, the fasteners will be described in terms of adhesive attachment means.

The adhesive attachment means are respectively covered by removable release liners, central pad release liner and flap release liner, both designated 58. The pressure-sensitive adhesives should be covered with release liners 58 to keep the adhesives from sticking to extraneous surfaces prior to use. Suitable release liners are described in U.S. Pat. No. 4,917,697.

The flaps 24 shown are integral with the main body portion 22. In such a case, the topsheet 40 forms one surface of both the flaps 24 and the main body portion 22, and the backsheet 42 may form the other surface of the same. In addition, the absorbent material of the sanitary napkin 20 may extend into the flaps 24 to form a flap absorbent core, as described in greater detail in U.S. Pat. No. 4,917,697. Alternatively, the flaps may be comprised of separate pieces of material which are attached to the main body portion 22, as described in EP 606 358 B1.

The flaps 24 are each associated with main body portion 22 along a juncture. This is typically a longitudinally-oriented (or "longitudinal") juncture, such as lines of juncture 30. As used herein, the terms "juncture" (or "line of juncture") refer to regions where the flaps 24 extend from or are joined to the main body portion 22. These regions can be any of various curved or straight lines, but they are not limited to lines. Thus, these regions can comprise flanges, strips, intermittent lines, and the like. In the embodiment illustrated in FIG. 1, line of juncture 30 is a curved line.

The flaps 24 have a proximal edge 32 adjacent the line of juncture 30. A distal edge (or "free end") 34 is remote from the line of juncture 30. As shown in FIG. 1, each flap 24 is divided into a front half 26, and a back half 28 by a flap transverse centerline T1. The flap transverse centerline T1 may coincide with the principal transverse centerline T of the sanitary napkin, but this is not absolutely required. The flap transverse centerline T1 extends through the principal longitudinal centerline L.

The sanitary napkin 20 can be divided into a front area 100 and a rear area 110, the front and rear areas divided by the flap transverse centerline T1. The front area 100 refers to the portion of the sanitary napkin 20 that is oriented towards the wearer's front when the sanitary napkin 20 is worn. The rear area 110 refers to the portion of the sanitary napkin 20 that is oriented towards the wearer's rear when the sanitary napkin 20 is worn.

The sanitary napkin 20 can have a front end 130 and a rear end 140. The front end 130 and the rear end 140 are generally disposed along the principal longitudinal centerline. The front end 130 refers the end of the sanitary napkin 20 that is oriented towards the wearer's front when the sanitary napkin is worn. The rear end 140 refers to the portion of the sanitary napkin 20 that is oriented towards the wearer's rear when the sanitary napkin 20 is worn.

The overall size of the flaps 24 can be readily selected by those skilled in the art. Preferably, the flaps 24 are sized so that the sanitary napkin 20 is from about 10 to about 23 centimeters wide between the distal edges 34 of the flaps at their greatest separation. Preferably each flap 24 is from about 5 to at least about 19 centimeters long in the direction parallel to the principal longitudinal centerline L of the sanitary napkin.

The shape of the flaps 24 can be selected by those skilled in the art. Preferably, not only are the flaps 24 mirror images of each other, the two halves of each flap 26 and 28 are also symmetrical about the flap transverse centerline T1. (It should be understood that the shape and orientation of the flaps described herein are those of a preferred embodiment. They are not mandatory design features.)

In the embodiment illustrated in FIG. 1, the flaps 24 are positioned slightly forward of the principal transverse centerline T of the sanitary napkin. (In such a case, the flap transverse centerline T1 does not coincide with the principal transverse centerline T of the sanitary napkin 20.) The flaps 24 can be positioned five to twenty millimeters forward of the principal transverse centerline T of the sanitary napkin. The flaps 24, however, are preferably evenly spaced from the principal longitudinal centerline T of the sanitary napkin.

The flaps 24 can be associated with the main body portion 22 in a number of different manners. Many of the different ways a component (such as the flaps 24) can be "joined to" or "associated with", etc. another component which are set forth in the definitions of these terms contained in U.S. Pat. No. 5,007,906 entitled "Decoupled Sanitary Napkin" which issued to Osborn, et al. on Apr. 16, 1991. When the flaps comprise separate elements, they can be joined to the main body portion 22 by any techniques known to those skilled in the art. Such techniques include, but are not limited to adhesives, heat and/or pressure, ultrasonics, etc.

The flaps 24 are associated with the main body portion 22 along lines of juncture 30. The lines of juncture can be concave, straight, (or, but preferably not convex) relative to the principal longitudinal centerline L. The lines of juncture 30 may comprise those lines or areas where separate flap elements are joined to the main body portion 24. Alternatively, when the flaps 24 are integral with the main body portion 22, the lines of juncture 30 may represent lines of demarcation between the main body portion 22 and the flaps 24 (although it is not necessary that there be a precise line of demarcation).

It is also not necessary that the flaps 24 extend from (or be joined along) the longitudinal edges 22 of the main body portion 22. The flaps 24 can be joined inward (or "inboard") from the longitudinal edges 80 toward the longitudinal centerline such as is shown in U.S. Pat. No. 4,900,320 issued to McCoy on Feb. 13, 1990. The flaps 24 can thus each be joined to the main body portion 22 along the principal longitudinal centerline L, or along the longitudinal edges 80 of the main body portion 22, or at any place between the principal longitudinal centerline L and the longitudinal edges 80 of the main body portion 22. The flaps 24 will, of course, generally be on opposite sides of the principal longitudinal centerline L.

The flaps 24 have a notch 50 and a first zone of anisotropic stiffness 70. The notch 50 is positioned remote from the line of juncture 30. In the embodiment shown in FIG. 1, the notch 50 is positioned along the distal edge 34 and centered on the flap transverse centerline T1. Without being bound by theory, it is believed that the notch 50 helps the flaps 24 fit around the edges of the wearer's panty.

The notch 50 may be either a slit or a notch. As used herein, the term "notch" refers to a space, indentation, or hollow along the edge of a material or a laminate of materials. As used herein the term "slit" refers to a narrow cut wherein two edges of material are adjacent or nearly adjacent one another without being joined to one another. A slit may be either linear or curvilinear.

The first zone of anisotropic stiffness 70 is contiguous with the notch 50. In the embodiment shown in FIG. 1, the flaps 24 each have two first zones of anisotropic stiffness 70 contiguous with the notch 50. The two first zones of anisotropic stiffness 70 are spaced from one another on opposite sides of the flap transverse centerline T1. While a pair of first zones of anisotropic stiffness 70 contiguous with the notch 50 is preferred, other embodiments, having a single first zone of anisotropic stiffness 70 contiguous with the notch 50 may also be used. Other embodiments having three or more first zone of anisotropic stiffness 70 contiguous with the notch 50 may also be used.

In the embodiment shown in FIG. 1, a first zone of anisotropic stiffness 70 is positioned on either side of the flap transverse centerline T1. Thus one first zone of anisotropic stiffness 70 resides on the front half 26 of flap 24 while the other first zone of anisotropic stiffness 70 resides on the back half 28 of flap 24.

The first zone of anisotropic stiffness 70 comprises a zone in which the stiffness of the material from which the flaps 24 are constructed has stiffness in one in-plane direction that differs from the stiffness in another in-plane direction. An example of a material having anisotropic stiffness is corrugated cardboard. Corrugated cardboard is stiffer in a direction in line with the lines of corrugation than in a direction cross plane to the lines of corrugation.

The anisotropic stiffness referred to herein is preferably elasticless. That is, it is accomplished without the use of separate elastic pieces, strands, or materials to stiffen one or more portions of the sanitary napkin.

Suitable structures for first zones of anisotropic stiffness are zones of material that are corrugated or ring rolled. Without being bound by theory, it is believed that the material between the fold lines acts as a beam that can have bending stiffness. The fold lines can be curved. Ring rolled or corrugated material has anisotropic stiffness in that the ring rolled or corrugated material is relatively stiffer in a direction in line with the lines and relatively less stiff in a direction crossing the lines of corrugation. The stiffer direction can be referred to as the stronger direction and the direction cross plane to the fold lines or lines of corrugation that is less stiff can be referred to as the weaker direction. The relatively stiffer direction can be orthogonal to the relatively less stiff direction but the angle of anisotropy can be any angle.

Suitable processes for ring rolling or corrugating are described in U.S. Pat. No. 4,107,364 issued to Sisson on Aug. 15, 1978, U.S. Pat. No. 4,834,741 issued to Sabee on May 30, 1989, U.S. Pat. No. 5,167,897 issued to Weber et al. on Dec. 1, 1992, U.S. Pat. No. 5,156,793 issued to Buell et al. on Oct. 20, 1992, and U.S. Pat. No. 5,143,679 issued to Weber et al. on Sep. 1, 1992.

Figure 4:
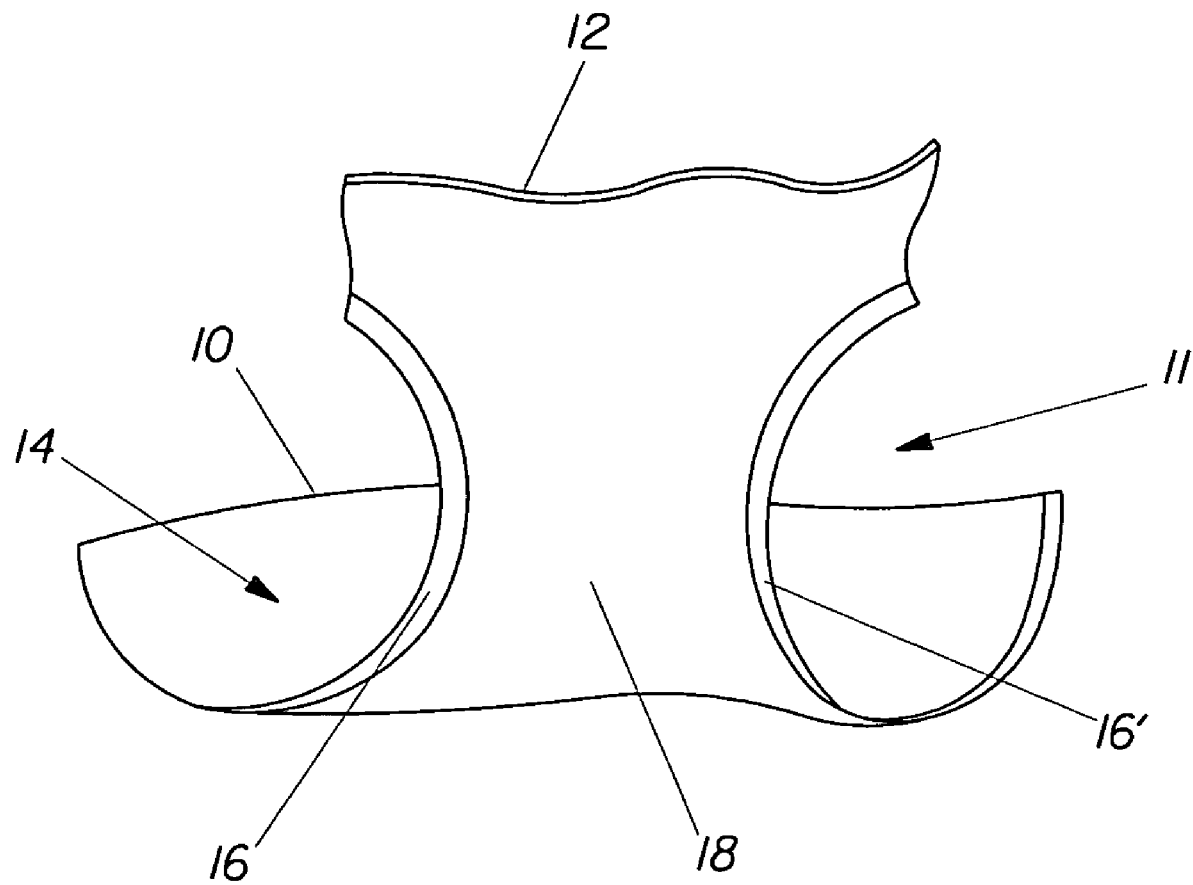
FIG. 4 is a perspective view of the crotch portion of a woman's panties.

FIG. 4 is a depiction of the crotch portion 14 of an undergarment 11 of the type commonly worn by many women and well known as a panty. A panty 11 comprises a front section 10, a back section 12, and a crotch portion 14 which joins the front and back sections. The crotch portion 14 comprises two side edges 16 and center crotch portion 18.

The sanitary napkin 20 of the present invention is utilized by removing the release liners 58 and placing the sanitary napkin 20 in a panty 11. The center of main body portion 22 is placed in crotch portion 14 of the panty with one end of main body portion 22 extending towards the front section 10 of the panty and the other end towards the back section 12. The backsheet 42 is placed in contact with the inner surface of center crotch portion 18 of the panty. Central pad adhesive 54 maintains the main body portion 22 in position.

The distal portions of flaps 24 are folded around the side edges 16 of the panty. The flap adhesives secure the flaps 24 to the underside of the panty. To fold a flap 24, the wearer pushes a portion of the flap 24 down around the edge 16 of the crotch portion 14 of the panty. Force is required to push the flap 24 from the body side of the panty to the underside of the panty because the flap must be bent to follow the arc formed by the edges 16 of the crotch portion 14.

The topsheet 40 can form one surface of the flaps 24 and the backsheet 42 can form the other surface of the flaps 24. The topsheet 40 and backsheet 42 are preferably flexible to allow the materials to conform to the wearer's body and panty, respectively. Thus, when the wearer pushes on a portion of the flap 24 to fold the flap 24 to the underside of the panty, the force applied by the wearer may not be transmitted throughout the entire flap 24. When the force applied by the wearer is not transmitted throughout the entire flap 24, only portions of the flap 24 may fold under the panty, leaving other portions of the flap on the body side of the panty. Because the flaps 24 have an adhesive attachment, portions of the flap 24 may be adhered to the underside of the panty while other portions of the flap 24 are not in the proper position. The wearer then can apply force to the other unattached portions of the flap 24 to attach those portions to the panty. This multi-step process that is sometimes used by wearer's to attach a flap 24 to the wearer's panty can be inconvenient to the wearer and can result in bunching and wadding of the flap 24, improper location of the sanitary napkin 20 relative to the wearer's body, and failure of the flap 24 to securely attach the sanitary napkin 20 to the wearer's panty.

To provide for flaps 24 that can be folded as a single unit and have the desired ability to relieve stresses developed as a result of folding the flap beneath the wearer's panty, the flaps 24 are provided with one or more zones of anisotropic stiffness 70 to distribute the force applied by the wearer to the flap 24 across more of the area of the flap 24.

The notch 50 and the first zone of anisotropic stiffness 70 are located in the flaps 24 remote from the line of juncture 30. As mentioned earlier, the notch 50 may be either a slit or a notch. The slit or notch may be of any shape. The overall dimension of the notch 50 can vary widely. Preferably, the notch 50 is not so large that it extends to the line of juncture 30.

The first zone of anisotropic stiffness 70 is contiguous with the notch 50. The first zone of anisotropic stiffness 70 comprises a zone of anisotropic stiffness. The zone of anisotropic stiffness may be of any shape. Typically, it will form a three-sided figure (roughly triangular, pie-shaped, or fan-shaped) in plan view. It should be understood, however, that the precise shape of the zone of anisotropic stiffness is not always as critical as the location and stiffness properties of the zone of anisotropic stiffness. Likewise, it is not critical for there to be precise lines of demarcation that mark the boundaries of the zones of anisotropic stiffness. Thus, there can be a gradual transition between the zones of anisotropic stiffness and the remainder of the flap.

The first zones of anisotropic stiffness are typically bounded on one side by at least a portion of the distal edge 34 of the flap 24. This is often a curved line. The remaining sides of the first zones of anisotropic stiffness are typically found within the remainder of the flap 24 and do not extend into the main body portion 22.

The total area covered by the first zones of anisotropic stiffness can vary widely. The area can cover a relatively large portion of the flap 24, provided there remain some portions of the flap 24 that are less stiff.

The stiffness of the first zones of anisotropic stiffness can vary depending on a number of factors. These include, but are not limited to the size and configuration of the wearer's panties, the size and configuration of the flaps, and the type of materials the flaps are made of. Any amount of stiffness can provide some benefit versus a sanitary napkin that is not provided with zones of anisotropic stiffness. The stiffness of the first zones of anisotropic stiffness should not be so great, however, that the stiffness causes the sanitary napkin to be uncomfortable to wear or to fit sloppily to the wearer's panties.

The first zone of anisotropic stiffness 70 can be provided with anisotropic stiffness by ring rolling these regions in accordance with the earlier-described ring rolling patents. The ring rolling or corrugating should be applied so that the fold lines 60 in the corrugations are oriented in a direction parallel with an angle fifteen to forty five degrees off of the flap transverse centerline on the side on which the first zone of anisotropic stiffness is located. More preferably, the ring rolling or corrugating should be applied so that the fold lines 60 in the corrugations are oriented in a direction parallel with an angle twenty to forty degrees off of the flap transverse centerline on the side on which the first zone of anisotropic stiffness is located. Even more preferably, the ring rolling or corrugating should be applied so that the fold lines 60 in the corrugations are oriented in a direction parallel with an angle twenty five to thirty five degrees off of the flap transverse centerline on the side on which the first zone of anisotropic stiffness is located. Most preferably, the ring rolling or corrugating should be applied so that the fold lines 60 in the corrugations are oriented in a direction parallel with an angle thirty degrees off of the flap transverse centerline on the side on which the first zone of anisotropic stiffness is located. The vertex of the angle is the intersection of the longitudinal centerline and the flap transverse centerline and the rotation of the angle is measured towards the longitudinal centerline in the area in which the first zone of anisotropic stiffness is located. Without being bound by theory, it is believed that by orienting the first zone of anisotropic stiffness in this manner, force applied by the wearer to a half of the flap having a first zone of anisotropic stiffness is transferred to the other half of the flap and the flap folds underneath the panty as a single unit.

The amount of stiffness provided can be varied throughout different portions of the first zone of anisotropic stiffness. For instance, the number or amplitude of the corrugations formed by the ring rolling could be varied so that either or both of these characteristics are greater closer to the flap transverse centerline T1.

The stress release means can be a notch in the flap, extension of the ring rolled material in a direction perpendicular to the fold lines, combinations of the two, or any other structure capable of providing for release of stress.

Figure 5:
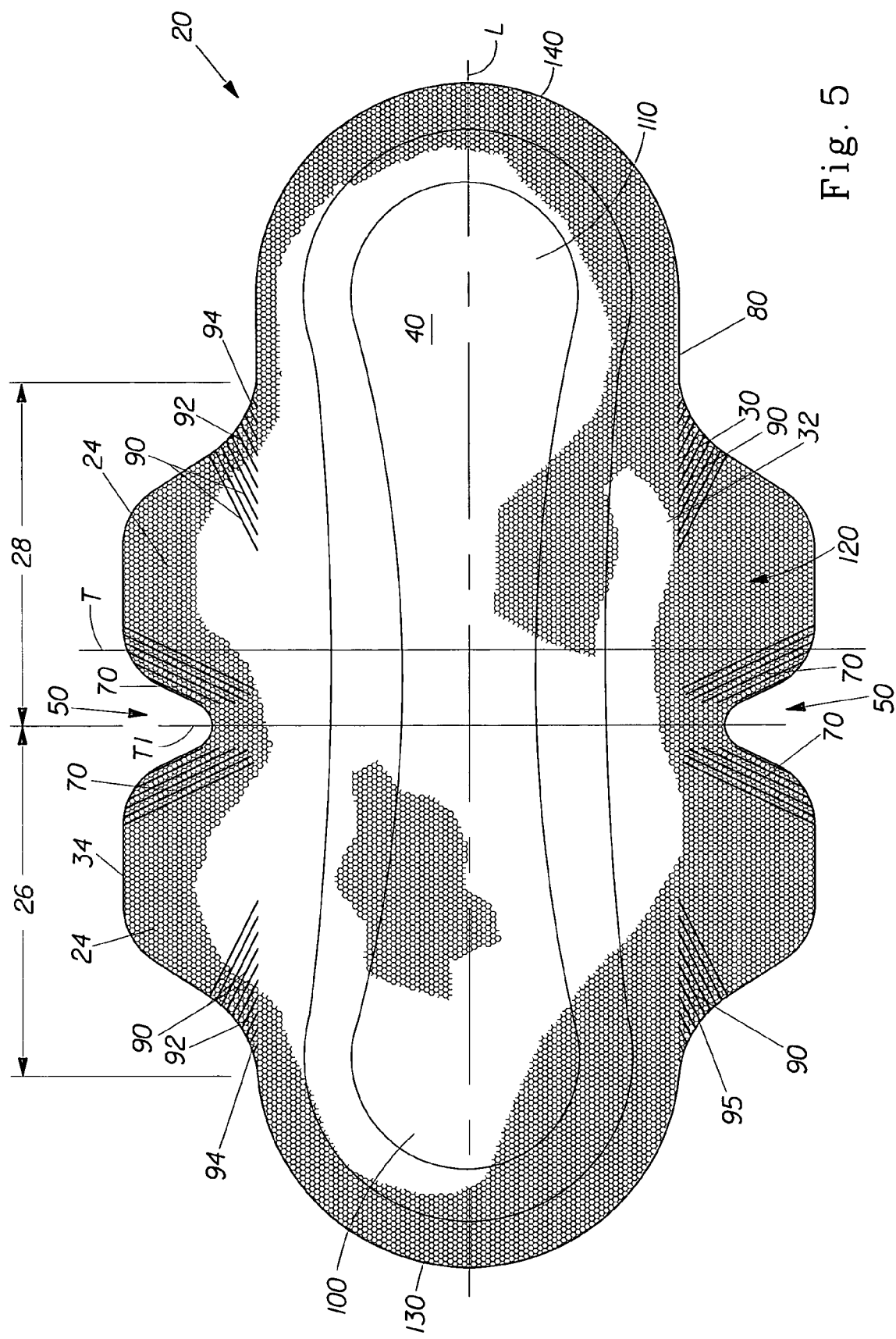
FIG. 5 is a top plan view of an alternative embodiment of a sanitary napkin of the present invention.
Figure 6:
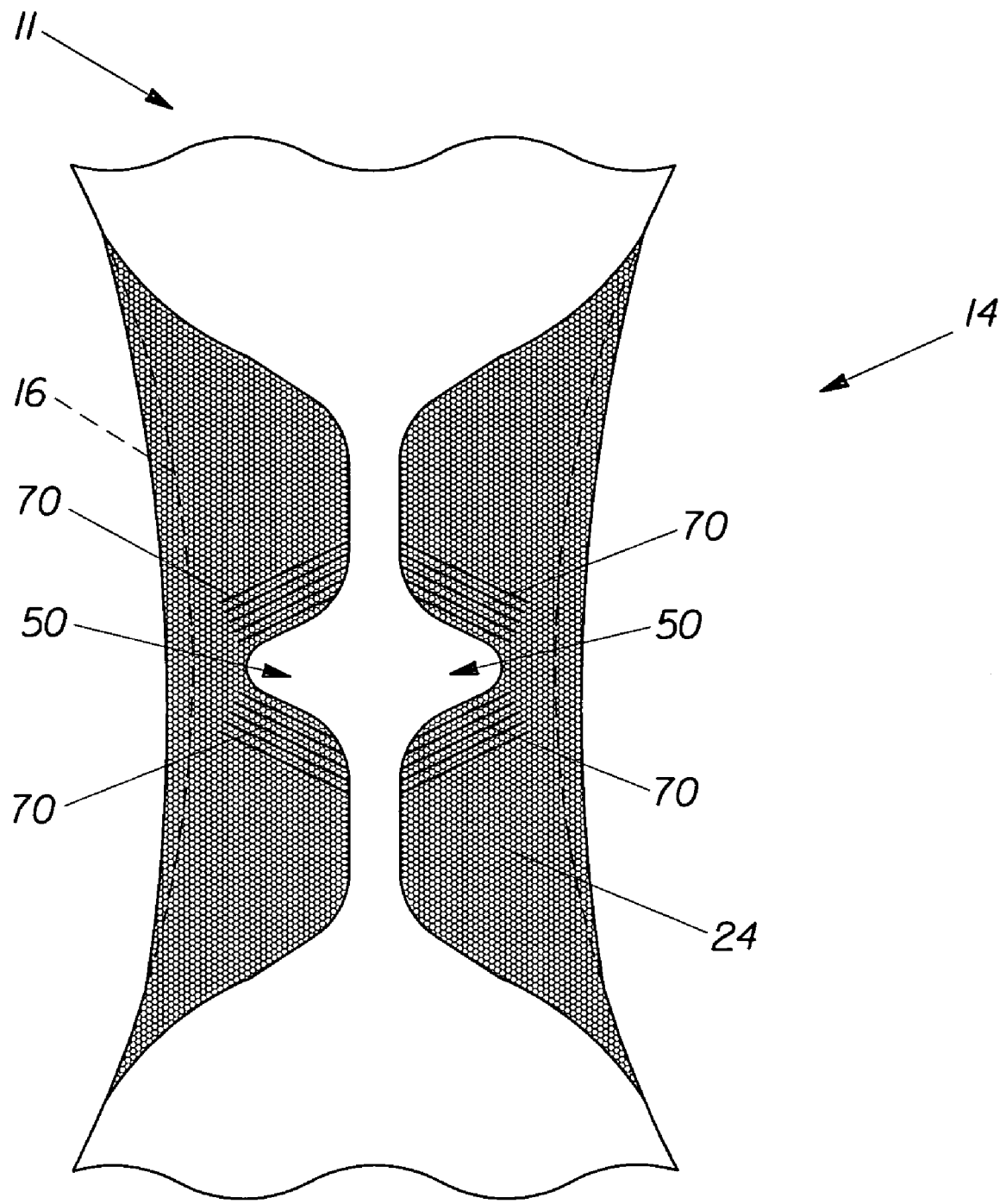
FIG. 6 is a bottom plan view of the sanitary napkin of FIG. 1 applied to a woman's panties.

FIG. 5 is an alternative embodiment of a sanitary napkin of the present invention having second zones of anisotropic stiffness 90. The second zones of anisotropic stiffness 90 can comprise portions of the main body portion 22, portions of the flaps 24, or both. The second zones of anisotropic stiffness 90 can be entirely on the flaps 24.

The second zones of anisotropic stiffness 90 are more specifically located in the corner regions 92 of the sanitary napkin 20. The sanitary napkin 20 preferably has four corner regions 92, two by each flap 24. The term "corner regions" 92, as used herein, refers to portions of the sanitary napkin 20 that are generally located along or adjacent a portion of the longitudinal juncture of each flap 24. The corner regions 92 for each flap 24 are located in two areas in the regions of the ends 94 of each juncture 30. One corner region 92 is located adjacent the longitudinal juncture 30 in the front half 26 of the flap 24. The other is adjacent the longitudinal juncture 30 in the back half 28 of the flap 24. The corner regions 92 are preferably at least partially disposed longitudinally away from the flap transverse centerline T1 in each direction. (Thus, the corner regions 92 may be described as being longitudinally "remote" from the flap transverse centerline T1.)

In the most preferred case (as will be subsequently described in greater detail), the second zones of anisotropic stiffness 90 are located along a portion of the bending line where the flaps 24 are folded around the wearer's panty crotch. The bending line will typically be located along or adjacent the longitudinal juncture 30 of each flap 24. Since the terms "portions", "zones", and "regions", as used herein, refer to general areas, the second zones of anisotropic stiffness 90 and the corner regions 92 are, thus, not limited to points which lie precisely on the lines of juncture 30. Typically, they will include both those points which lie on the lines of juncture 30 as well as the surrounding areas of the sanitary napkin 20 (which include the aforementioned bending lines). The longitudinal junctures, thus, typically serve as good approximations for the location of the second zones of anisotropic stiffness 90.

The corner regions 92 are designated as such because they typically include the "corners" formed along the periphery of the sanitary napkin 20. The "corners" occur where the edges 95 of the flaps 24 intersect with the longitudinal side edges 80 of the main body portion 22 when the sanitary napkin 20 is shown in a plan view. It is not necessary for there to be a sharp angle formed at the intersection of these edges, or for lines of demarcation to designate the same, however.

The second zones of anisotropic stiffness 90 may be of any shape. Typically, they will form a three-sided figure (roughly triangular, pie-shaped, or fan-shaped) in plan view when they are fully extended. Often, the figure defined by the second zones of anisotropic stiffness will have two sides that are of approximately equal length and a shorter side. The edge 35 of the flaps 24 usually forms the shorter side. It should be understood, however, that the precise shape of the second zones of anisotropic stiffness 90 is not always as critical as the location and stiffness properties of the second zones of anisotropic stiffness. Likewise, it is not critical for there to be precise line of demarcation that marks the boundaries of the second zones of anisotropic stiffness 90. Thus, there can be a gradual transition between the second zones of anisotropic stiffness 90 and the other portions of the sanitary napkin.

The second zones of anisotropic stiffness 90 may be bounded on one side by the line of juncture 30. Alternatively, the boundary may be adjacent the line of juncture 30. If the second zones of anisotropic stiffness 90 are provided in the main body portion 22 (for instance, if they are formed by a fold made through the main body portion 22) the boundary may be as far inboard as the principal longitudinal centerline L. The second zones of anisotropic stiffness 90 are typically bounded at the ends by at least a portion of the edge 35 of the flap 24. This is often a curved line. The second zones of anisotropic stiffness 90 can also be bounded at the ends by a portion of the longitudinal edges 80 of the main body portion and/or end edges 82 of the main body portion 22. The third side of the second zones of anisotropic stiffness is typically formed by a boundary which may be an imaginary line that runs from the point of the second zones of anisotropic stiffness 90 which is either located on the flap transverse centerline T1 (or nearest to the same), to a point on the edge 35 of the flap 24.

The total area covered by the second zones of anisotropic stiffness 90 can vary widely. The area can cover a relatively large portion of the sanitary napkin, provided there remain some portions of the sanitary napkin adjacent at least portions of the principal longitudinal centerline and the flap transverse centerline that are less stiff. The second zones of anisotropic stiffness 90 can be provided along the entire juncture 30 of the flaps 24 with the main body portion 22. Preferably, in the present invention, second zones of anisotropic stiffness 90 are not provided either along the entire juncture 30 or throughout the entire flap.

Suitable structures for second zones of anisotropic stiffness are the same as those described for first zones of anisotropic stiffness. The ring rolling or corrugating for the second zones of anisotropic stiffness can be applied so that the fold lines 60 in the corrugations are oriented in a direction parallel with an angle fifty to eighty three degrees off of the flap transverse centerline on the side on which the second zone of anisotropic stiffness is located. More preferably, the ring rolling or corrugating should be applied so that the fold lines 60 in the corrugations are oriented in a direction parallel with an angle fifty seven to seventy eight degrees off of the flap transverse centerline on the side on which the second zone of anisotropic stiffness is located. Even more preferably, the ring rolling or corrugating should be applied so that the fold lines 60 in the corrugations are oriented in a direction parallel with an angle sixty to seventy three degrees off of the flap transverse centerline on the side on which the second zone of anisotropic stiffness is located. The vertex of the angle is the intersection of the longitudinal centerline and the flap transverse centerline and the rotation of the angle is measured towards the longitudinal centerline in the area in which the second zone of anisotropic stiffness is located. Without being bound by theory, it is believed that by orienting the second zone of anisotropic stiffness in this manner, the flap material is less stiff in a direction generally perpendicular to the desired bending line of the flap which is the panty line in the wearer's crotch region. Thus, when the wearer applies the force necessary to wrap a flap beneath her panty, the flap is less stiff in the direction of desired bending and deforms in a manner such that the bending line is nearly compliant with the panty line. The stress release means can be extension of the ring rolled material in a direction perpendicular to the fold lines or any other structure capable of providing for release of stress.

If a second zone of anisotropic stiffness is located in the front area of the sanitary napkin 20, the ring rolling or corrugating for the second zones of anisotropic stiffness is best applied so that the fold lines 60 in the corrugations are oriented in a direction parallel with an angle sixty three to eighty three degrees off of the flap transverse centerline on the side on which the second zone of anisotropic stiffness is located. More preferably, the ring rolling or corrugating should be applied so that the fold lines 60 in the corrugations are oriented in a direction parallel with an angle sixty eight to seventy eight degrees off of the flap transverse centerline on the side on which the second zone of anisotropic stiffness is located. Most preferably, the ring rolling or corrugating should be applied so that the fold lines 60 in the corrugations are oriented in a direction parallel with an angle seventy three degrees off of the flap transverse centerline on the side on which the second zone of anisotropic stiffness is located. Without being bound by theory, it is believed that by orienting a second zone of anisotropic stiffness in the front area of the sanitary napkin 20 in this manner, the flap material is less stiff in a direction generally perpendicular to the desired bending line of the flap which is the panty line in the wearer's crotch region. Thus, when the wearer applies the force necessary to wrap a flap beneath her panty, the flap is less stiff in the direction of desired bending and deforms in a manner such that the bending line is nearly compliant with the panty line.

If a second zone of anisotropic stiffness is located in the back area of the sanitary napkin 20, the ring rolling or corrugating for the second zone of anisotropic stiffness is best applied so that the fold lines 60 in the corrugations are oriented in a direction parallel with an angle forty five to seventy five degrees off of the flap transverse centerline on the side on which the second zone of anisotropic stiffness is located. More preferably, the ring rolling or corrugating should be applied so that the fold lines 60 in the corrugations are oriented in a direction parallel with an angle fifty to seventy degrees off of the flap transverse centerline on the side on which the second zone of anisotropic stiffness is located. Even more preferably, the ring rolling or corrugating should be applied so that the fold lines 60 in the corrugations are oriented in a direction parallel with an angle fifty five to sixty five degrees off of the flap transverse centerline on the side on which the second zone of anisotropic stiffness is located. Most preferably, the ring rolling or corrugating should be applied so that the fold lines 60 in the corrugations are oriented in a direction parallel with an angle sixty degrees off of the flap transverse centerline on the side on which the second zone of anisotropic stiffness is located. Without being bound by theory, it is believed that by orienting a second zone of anisotropic stiffness in the rear area of the sanitary napkin 20 in this manner, the flap material is less stiff in a direction generally perpendicular to the desired bending line of the flap which is the panty line in the wearer's crotch region. Thus, when the wearer applies the force necessary to wrap a flap beneath her panty, the flap is less stiff in the direction of desired bending and deforms in a manner such that the bending line is nearly compliant with the panty line.

Different orientations for the second zones of anisotropic stiffness can be desirable because a panty can have panty lines that are asymmetric between the front and back of the panty. A panty can be asymmetric between the front and back to allow for the panty to better fit the wearer's body in the crotch region, which is also asymmetric between the front and back.

The stiffness of the second zones of anisotropic stiffness can vary depending on numerous factors. These include, but are not limited to the size and configuration of the wearer's panties, the size and configuration of the flaps, and the type of materials the flaps are made of. Any amount of stiffness can provide some benefit versus a sanitary napkin that is not provided with zones of anisotropic stiffness. The stiffness of the second zones of anisotropic stiffness should not be so great, however, that the stiffness causes the sanitary napkin to be uncomfortable to wear or to fit sloppily to the wearer's panties.

A flap 24 having indicia 120 indicating a location where a force can be applied by the wearer to engage the flap 24 is shown in FIG. 5. Indicia 120 can help the wearer identify the proper location on the flap 24 to push the flap 24 so that the entire flap 24 folds beneath the panty as a single unit. Indicia 120 can be located on the front half 26 of the flap 24, the back half 28 of the flap 24, or on both the front half 26 and the back half 28 of the flap 24. Preferably, indicia are located on both flaps 24.

Thus, the present invention relates to absorbent articles such as sanitary napkins having flaps with a notch and a first zone of anisotropic stiffness for assisting in transferring the force applied by the wearer through the flaps when the flaps are folded down and under a wearer's undergarment and attached to the underside of the undergarment.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for wearing in an undergarment, said absorbent article having a principal longitudinal centerline, a transverse centerline, and a flap transverse centerline, said principal longitudinal centerline and said flap transverse centerline having an intersection, a front area and a back area, said front and back areas divided by said flap transverse centerline, a left side and a right side, said left side and said right side generally disposed along said transverse centerline, said absorbent article comprising:

a main body portion having two spaced apart longitudinal side edges and two spaced apart transverse end edges, said main body portion comprising a liquid pervious top sheet, a liquid impervious backsheet joined to said topsheet and an absorbent core positioned between said topsheet and said backsheet;

a pair of flaps for folding around and securing said absorbent article to said undergarment, said flaps being associated with said main body portion at a juncture, with one flap extending laterally outward from each longitudinal side edge of said main body portion, each of said flaps having a front half and a back half, said front and back halves divided by said flap transverse centerline;

a notch located in said flaps remote from said juncture; and at least one first zone of anisotropic stiffness located in said flaps contiguous with said notch, wherein said first zone of anisotropic stiffness has a relatively stiffer direction and a relatively less stiff direction, wherein said relatively stiffer direction of said first zone of anisotropic stiffness is parallel with an angle fifteen to forty five degrees off of said flap transverse centerline on the side on which said first zone of anisotropic stiffness is located, wherein the vertex of said angle is said intersection of said longitudinal centerline and said flap transverse centerline, and the rotation of the angle is measured towards said longitudinal centerline in said area in which said first zone of anisotropic stiffness is located.

2. The absorbent article of claim 1 wherein said flap comprises a pair of first zones of anisotropic stiffness.

3. The absorbent article of claim 2 wherein said pair of first zones of anisotropic stiffness are spaced from one another.

4. The absorbent article of claim 1 wherein said first zone of anisotropic stiffness is made by pre-corrugated or ring rolled portions of said flap.

5. The absorbent article of claim 1 further comprising a second zone of anisotropic stiffness located adjacent said juncture, wherein said second zone of anisotropic stiffness has a relatively stiffer direction and a relatively less stiff direction, wherein said relatively stiffer direction of said second zone of anisotropic stiffness is parallel with an angle fifty to eighty three degrees off of said flap transverse centerline on the side on which said second zone of anisotropic stiffness is located, wherein the vertex of said angle is said intersection of said longitudinal centerline and said flap transverse centerline, and the rotation of the angle is measured towards said longitudinal centerline in said area in which said second zone of anisotropic stiffness is located.

6. The absorbent article of claim 5 wherein said second zone of anisotropic stiffness is made of corrugated or ring-rolled portions of said absorbent article.

7. The absorbent article of claim 1 wherein said flap has indicia indicating a location where a force can be applied to engage said flap.

8. The absorbent article of claim 1 wherein said flap transverse centerline is five to twenty millimeters from said transverse centerline.

9. An absorbent article for wearing in an undergarment, said absorbent article having a principal longitudinal centerline, a transverse centerline, and a flap transverse centerline, said principal longitudinal centerline and said flap transverse centerline having an intersection, a front area and a back area, said front and back areas divided by said flap transverse centerline, a left side and a right side, said left side and said right side generally disposed along said transverse centerline, said absorbent article comprising:
   a main body portion having two spaced apart longitudinal side edges and two spaced apart transverse end edges, said main body portion comprising a liquid pervious top sheet, a liquid impervious backsheet joined to said topsheet and an absorbent core positioned between said topsheet and said backsheet;
   a pair of flaps for folding around and securing said absorbent article to said undergarment, said flaps being associated with said main body portion at a juncture, with one flap extending laterally outward from each longitudinal side edge of said main body portion, each of said flaps having a front half and a back half, said front and back halves divided by said flap transverse centerline;
   a notch located in said flaps remote from said juncture; and
   a pair of first zones of anisotropic stiffness located in said flaps spaced from one another and contiguous with said notch, wherein said first zone of anisotropic stiffness has a relatively stiffer direction and a relatively less stiff direction, wherein said relatively stiffer direction of said first zone of anisotropic stiffness is parallel with an angle fifteen to forty five degrees off of said flap transverse centerline on the side on which said first zone of anisotropic stiffness is located, wherein the vertex of said angle is said intersection of said longitudinal centerline and said flap transverse centerline, and the rotation of the angle is measured towards said longitudinal centerline in said area in which said first zone of anisotropic stiffness is located.

10. The absorbent article of claim 9 wherein said first zone of anisotropic stiffness is made by pre-corrugated or ring rolled portions of said flap.

11. The absorbent article of claim 9 further comprising a second zone of anisotropic stiffness located adjacent said juncture, wherein said second zone of anisotropic stiffness has a relatively stiffer direction and a relatively less stiff direction, wherein said relatively stiffer direction of said second zone of anisotropic stiffness is parallel with an angle fifty to eighty three degrees off of said flap transverse centerline on the side on which said second zone of anisotropic stiffness is located, wherein the vertex of said angle is said intersection of said longitudinal centerline and said flap transverse centerline, and the rotation of the angle is measured towards said longitudinal centerline in said area in which said second zone of anisotropic stiffness is located.

12. The absorbent article of claim 11 wherein said second zone of anisotropic stiffness is made of corrugated or ring-rolled portions of said absorbent article.

13. The absorbent article of claim 9 wherein said flap has indicia indicating a location where a force can be applied to engage said flap.

14. The absorbent article of claim 9 wherein said flap transverse centerline is five to twenty millimeters from said transverse centerline.

15. An absorbent article for wearing in an undergarment, said absorbent article having a principal longitudinal centerline, a transverse centerline, and a flap transverse centerline, said principal longitudinal centerline and said flap transverse centerline having an intersection, a front area and a back area, said front and back areas divided by said flap transverse centerline, a left side and a right side, said left side and said right side generally disposed along said transverse centerline, said absorbent article comprising:
   a main body portion having two spaced apart longitudinal side edges and two spaced apart transverse end edges, said main body portion comprising a liquid pervious top sheet, a liquid impervious backsheet joined to said topsheet and an absorbent core positioned between said topsheet and said backsheet;
   a pair of flaps for folding around and securing said absorbent article to said undergarment, said flaps being associated with said main body portion at a juncture, with one flap extending laterally outward from each longitudinal side edge of said main body portion, each of said flaps having a front half and a back half, said front and back halves divided by said flap transverse centerline;
   a notch located in said flaps remote from said juncture;
   a pair of first zones of anisotropic stiffness located in said flaps spaced from one another and contiguous with said notch, wherein said first zone of anisotropic stiffness has a relatively stiffer direction and a relatively less stiff direction, wherein said relatively stiffer direction of said first zone of anisotropic stiffness is parallel with an angle fifteen to forty five degrees off of said flap transverse centerline on the side on which said first zone of anisotropic stiffness is located, wherein the vertex of said angle is said intersection of said longitudinal centerline and said flap transverse centerline, and the rotation of the angle is measured towards said longitudinal centerline in said area in which said first zone of anisotropic stiffness is located; and
   a second zone of anisotropic stiffness located adjacent said juncture, wherein said second zone of anisotropic stiffness has a relatively stiffer direction and a relatively less stiff direction, wherein said relatively stiffer direction of said second zone of anisotropic stiffness is parallel with an angle fifty to eighty three degrees off of said flap transverse centerline on the side on which said second zone of anisotropic stiffness is located, wherein the vertex of said angle is said intersection of said longitudinal centerline and said flap transverse centerline, and the rotation of the angle is measured towards said longitudinal centerline in said area in which said second zone of anisotropic stiffness is located.

16. The absorbent article of claim 15 wherein said first zone of anisotropic stiffness is made by pre-corrugated or ring rolled portions of said flap.

17. The absorbent article of claim 15 wherein said second zone of anisotropic stiffness is made by pre-corrugated or ring rolled portions of said flap.

18. The absorbent article of claim 15 wherein said flap has indicia indicating a location where a force can be applied to engage said flap.

19. The absorbent article of claim 15 wherein said flap transverse centerline is five to twenty millimeters from said transverse centerline.

* * * * *